(12) United States Patent
Cranston et al.

(10) Patent No.: US 9,810,587 B2
(45) Date of Patent: Nov. 7, 2017

(54) COMPOSITE SENSOR FIBRES AND APPLICATIONS THEREFOR

(75) Inventors: Robin William Cranston, Clayton (AU); Ilias Louis Kyratzis, Clayton (AU); Lance Victor Nichols, Clayton (AU); Michael Shane O'Shea, Clayton (AU); Gary Peeters, Clayton (AU); Louise Catherine Van Der Werff, Clayton (AU)

(73) Assignee: Commonwealth Scientific and Industrial Research Organisation (AU)

( * ) Notice: Subject to any disclaimer, the term of this patent is extended or adjusted under 35 U.S.C. 154(b) by 363 days.

(21) Appl. No.: 14/382,633

(22) PCT Filed: Aug. 2, 2012

(86) PCT No.: PCT/AU2012/000916
§ 371 (c)(1),
(2), (4) Date: Sep. 3, 2014

(87) PCT Pub. No.: WO2013/131120
PCT Pub. Date: Sep. 12, 2013

(65) Prior Publication Data
US 2015/0088027 A1    Mar. 26, 2015

(30) Foreign Application Priority Data
Mar. 5, 2012    (AU) ................... 2012900852

(51) Int. Cl.
*G01K 11/00*    (2006.01)
*G01K 11/12*    (2006.01)
(Continued)

(52) U.S. Cl.
CPC ............... *G01K 11/12* (2013.01); *A61B 5/01* (2013.01); *A61B 5/445* (2013.01); *A61B 5/6802* (2013.01);
(Continued)

(58) Field of Classification Search
None
See application file for complete search history.

(56) References Cited

U.S. PATENT DOCUMENTS 3,651,695 A    3/1972    Brown
4,301,023 A *  11/1981   Schuberth ............ A61K 8/0295
                                                    252/299.7

(Continued)

FOREIGN PATENT DOCUMENTS

CN    1314994 A    9/2001
CN    202051689 U    11/2011
(Continued)

OTHER PUBLICATIONS

Chinese Office Action for Chinese Patent Application No. 201280072560.7 (mailed Mar. 1, 2016).
(Continued)

*Primary Examiner* — Erica Lin
(74) *Attorney, Agent, or Firm* — Merchant & Gould P.C.

(57) ABSTRACT

A composite sensor fiber comprising a filamentary core (12) and an outer layer (30) encapsulating an intermediate sensor layer (20) of a detectably thermoresponsive material. Also disclosed are a method of making composite sensor fibers, a dressing comprising a fabric having a matrix of the fibers, and a method of monitoring a wound that utilizes the dressing.

19 Claims, 3 Drawing Sheets

(51) Int. Cl.
*D01F 8/00* (2006.01)
*G01K 13/00* (2006.01)
*A61B 5/00* (2006.01)
*D01D 11/06* (2006.01)
*A61B 5/01* (2006.01)
*A61F 13/00* (2006.01)
*D04H 3/005* (2012.01)
*A61F 13/84* (2006.01)

(52) U.S. Cl.
CPC ........ *A61F 13/00059* (2013.01); *A61F 13/84* (2013.01); *D01D 11/06* (2013.01); *D01F 8/00* (2013.01); *D04H 3/005* (2013.01); *G01K 13/002* (2013.01); *A61F 2013/00953* (2013.01); *A61F 2013/8473* (2013.01)

(56) References Cited

U.S. PATENT DOCUMENTS

| | | |
|---|---|---|
| 4,433,637 A | 2/1984 | Buirley et al. |
| 4,510,188 A | 4/1985 | Ruggeri |
| 4,642,250 A | 2/1987 | Spector |
| 4,681,791 A | 7/1987 | Shibahashi et al. |
| 5,153,066 A | 10/1992 | Tanaka et al. |
| 5,181,905 A | 1/1993 | Flam |
| 5,361,320 A | 11/1994 | Liu et al. |
| 5,806,528 A | 9/1998 | Magliochetti |
| 6,004,691 A | 12/1999 | Eshraghi |
| 6,257,759 B1 | 7/2001 | Witonsky et al. |
| 6,444,313 B1 | 9/2002 | Ono et al. |
| 7,976,944 B2 | 7/2011 | Hu et al. |
| 8,029,190 B2 | 10/2011 | MacDonald et al. |
| 2002/0090510 A1 | 7/2002 | Ono et al. |
| 2003/0087566 A1 | 5/2003 | Carlyle et al. |
| 2005/0186877 A1* | 8/2005 | Yang .......................... B32B 5/26 442/327 |
| 2008/0279253 A1 | 11/2008 | MacDonald et al. |
| 2009/0046760 A1* | 2/2009 | Matheson ............ A41D 13/005 374/141 |
| 2009/0155496 A1 | 6/2009 | Wilderbeek et al. |
| 2011/0028804 A1 | 2/2011 | Jernigan |
| 2011/0068493 A1* | 3/2011 | Buyuktanir ...... B29D 11/00663 264/1.27 |

FOREIGN PATENT DOCUMENTS

| | | |
|---|---|---|
| EP | 0 430 608 A1 | 6/1991 |
| JP | 48-044522 | 6/1973 |
| JP | 59-144613 A | 8/1984 |
| JP | 4-756267 B2 | 8/2011 |
| WO | WO 2008/115682 A2 | 9/2008 |

OTHER PUBLICATIONS

Van Der Werff, et al., "Formation of Novel Composite Fibres Exhibiting Thermochromic Behaviour", *CAM Conference*, 13 pp. (2011).

Van Der Werff, et al., "Formation of a Novel Three-layered Composite Fibre Exhibiting Thermochromic Behaviour", *CAM Conference*, Abstract, 1 p. (2011).

Van Der Werff, et al., "Formation of Novel Composite Fibres Exhibiting Thermochromic Behaviour", *18th ICCM*, 5 pp. (Aug. 24, 2011).

Van Der Werff, et al., "Formation of Novel Composite Fibres Exhibiting Thermochromic Behaviour", *18th ICCM*, 9 pp. (Aug. 24, 2011)

www.freshscience.org, "A smart bandage reveals healing", *Fresh Science*, 1 p. (Jun. 5, 2011).

Van Der Werff, et al., "Thermal Mapping of Chronic Wounds using a Colour Changing System Incorporated into a Wound Dressing", *AWMA*, 1 p. (2010).

Van Der Werff, "Advanced Wound Dressings: Thermal Mapping of Chronic Wounds Using Thermochromics", *Phd Candidate Presentation*, 16 pp. (2011).

International Search Report for International Patent Application No. PCT/AU2012/000916 (mailed Sep. 14, 2012).

* cited by examiner

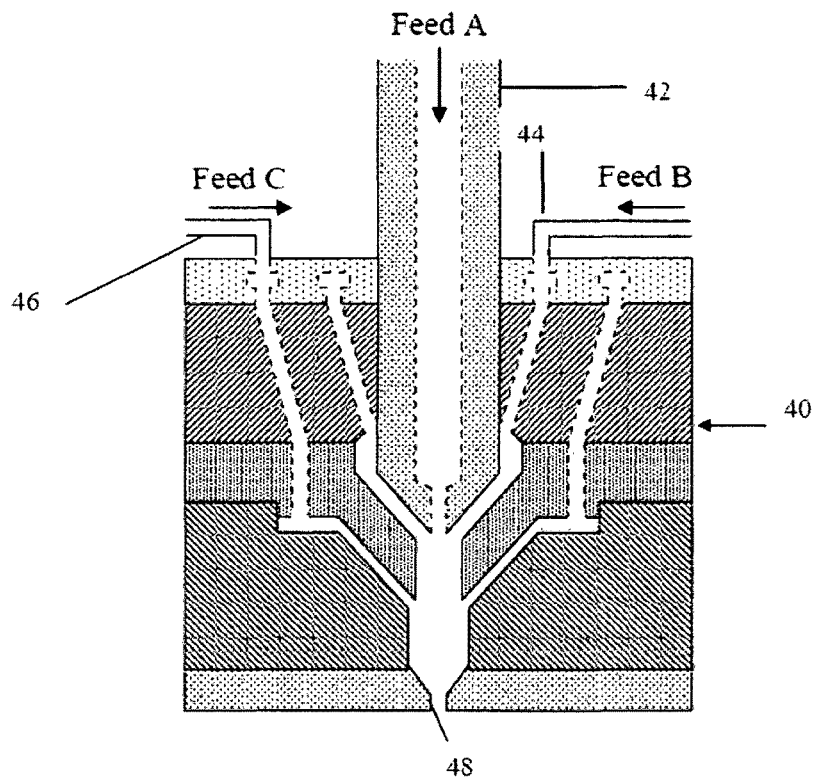
Figure 3
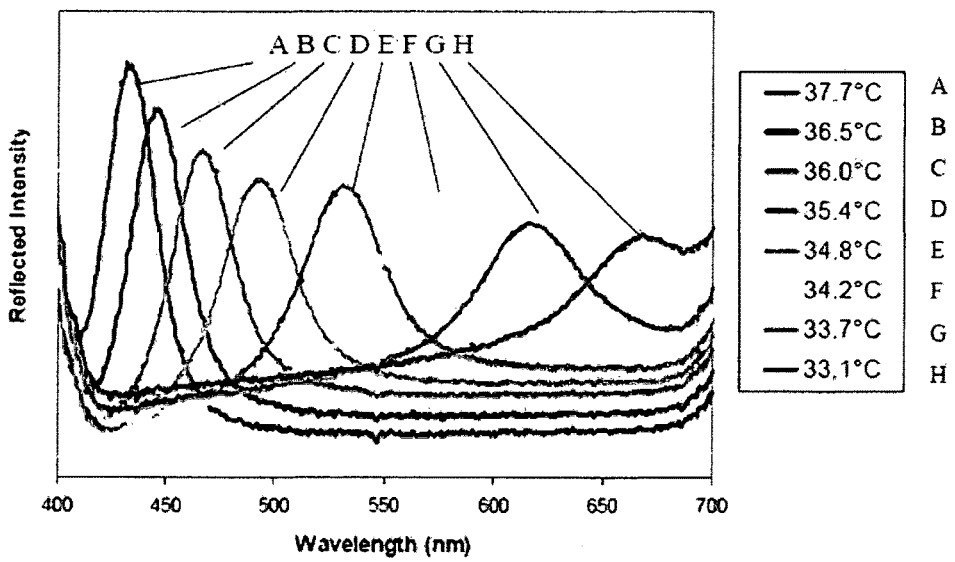
Figure 4 — The reflectance spectra in the visible range as a function of temperature for the composite fibres containing the liquid crystal mixture 2.

COMPOSITE SENSOR FIBRES AND APPLICATIONS THEREFOR

This application is a U.S. National Stage Application under 35 U.S.C. §371 of International Patent Application No. PCT/AU2012/000916 filed 2 Aug. 2012, which claims the benefit of priority to Australian Patent Application No. 2012900852 filed 5 Mar. 2012, the disclosures of all of which are hereby incorporated by reference in their entireties. The International Application was published in English on 12 Sep. 2013 as WO 2013/131120 A1. To the extent appropriate, a claim of priority is made to each of the above disclosed applications.

FIELD OF THE INVENTION

This invention relates generally to composite sensor fibres containing thermoresponsive material, and to methods of making such fibres. In a particularly advantageous application, the invention relates to composite thermochromic fibres and to fabrics or non-wovens incorporating such fibres. In one aspect, the invention is concerned with a dressing or other garment that includes the thermochromic fabric and provides a method of monitoring a wound in which such a dressing is applied to the wound. The composite sensor fibres of the invention can also be used for the monitoring of temperatures over engineering surfaces such as building elements (e.g. walls, floors and ceilings), wires, cables and pipes.

BACKGROUND OF THE INVENTION

A number of textile products have been described for applications including bedding, apparel, hygiene and toys in which microencapsulated thermochromic pigments are incorporated into synthetic fibres as a dispersed phase (e.g. U.S. Pat. No. 6,444,313 and US patent application 2003/0087566), or as a coating on the surfaces of the fibres using a binding medium (e.g. U.S. Pat. No. 4,681,791). Thermochromic yarns, fabrics and garments are also disclosed in Japanese patent publications 59144613 and 4756267. Japanese patent publication 48044522 discloses composite fibres containing cholesteric liquid crystals.

US patent application 2008/0279253 discloses thermochromic garments to track body temperature regulation of patients and children for use by clinicians, parents and caregivers. The garment contains at least two thermochromic dyes or colourants, each being sensitive to a different temperature range. This provides a facility to identify whether a body is overheating or is too cool, or to ascertain whether a heating or cooling device is working sufficiently. Described embodiments include the addition of mincroencapsulated leuco dyes into polymer fibrous webs by melt blowing techniques. Another garment incorporating thermochromic pigments or thermochromic strip thermometers is described in US patent application 2009/00467760. The garment is proposed as a means of providing early detection and prevention of cold exposure to skin surfaces, or venous insufficiencies.

There have been a range of disclosures of medical or clinical applications for thermochromic liquid crystalline materials. In U.S. Pat. No. 5,806,528, such materials are proposed as temperature indicators for fluids intravenously delivered to patients, to ensure that they are not at a temperature that is either uncomfortable or harmful to a patient. US patent application 2011/0028804 discloses a topical product that exhibits thermochromic behaviour when applied to the skin. The product is intended to be used for diagnosing the onset of conditions such as necrosis and decubitus ulcers in the skin of a patient, by identifying increased temperatures due to inflammation present in the early stages of ulcer formation. The topical product is described as being a liquid and is possibly applied as a spray. The patent application suggests the use of either liquid crystalline mixtures or leuco dyes as a thermochromic component, dispersed into a body lotion or soap.

U.S. Pat. No. 5,181,905 discloses a wound dressing containing a thermochromic indicator for monitoring the condition of an underlying wound while the dressing is being worn. The thermochromic component is in the form of a temperature sensitive liquid crystal tape that has a plurality of labelled boxes containing liquid crystalline mixtures tuned to appear coloured at different temperatures. Temperature determination is dependent on which box or boxes appear coloured while the dressing is being worn.

U.S. Pat. No. 4,433,637 describes a thin flexible sheet coated with liquid crystals, microencapsulated or otherwise, over a black backing as a means for measuring temperatures of the surface of the skin.

It is an object of the invention, at least in one or more aspects, to provide a novel and useful composite sensor fibre.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect, the invention provides a novel structure of composite sensor fibre that may be usefully adapted as a composite thermochromic fibre. In this aspect, the invention also provides a method of forming the composite sensor fibre.

A second aspect of the invention entails a realisation that a fabric or non-woven formed from composite thermochromic fibres may be effectively incorporated in a dressing by which the condition of an underlying wound may be monitored without the use of external electronics or temperature probes. In this aspect, the invention also provides a method of monitoring a wound.

In its first aspect, the invention provides a composite sensor fibre comprising a filamentary core and an outer layer encapsulating an intermediate sensor layer of a detectably thermoresponsive material.

In this aspect, the invention further provides a method of making the composite sensor fibre comprising continuously delivering the filamentary core from a supply thereof and co-extruding the thermoresponsive material about the core and the outer layer about the thermoresponsive material at a temperature that facilitates the coextrusion but at which the core remains substantially solid and the outer layer does not substantially inhibit delivery of the thermoresponsive material.

In an embodiment, the thermoresponsive material is a thermochromic material. Preferred thermochromic materials comprise thermochromic liquid crystalline materials, which may typically be mixtures of liquid crystalline compounds in order to achieve a predetermined temperature indication accuracy over a predetermined temperature range.

For thermochromic applications, the outer layer is generally transparent and the filamentary core is preferably configured to provide a contrast for facilitating the observation of temperature or temperature gradient changes in the thermochromic material, for example specific colour appearances or gradients. Advantageous embodiments of the filamentary core exhibit a generally circular or generally trilobal cross section.

The first aspect of the invention extends to materials, e.g. but not limited to fabrics, non-wovens and other fibrous materials, formed from or incorporating the composite sensor fibres of the invention.

In the second aspect of the invention, there is provided a dressing that includes a fabric having a matrix of thermochromic composite sensor fibres according to the first aspect of the invention, which fibres indicate localised body temperature changes adjacent the dressing by visibly exhibiting a change in colour or colour gradient.

In the second aspect, the invention further provides a method of monitoring a wound comprising applying to the wound a dressing that includes a fabric having a matrix of thermochromic composite sensor fibres according to the first aspect of the invention, which fibres indicate localised body temperature changes adjacent the dressing by visibly exhibiting a change in colour or colour gradient.

The thermochromic fibres of the second aspect of the invention are preferably composite sensor fibres according to the first aspect in which the intermediate sensor layer contains thermochromic material. For this application, the thermochromic material is preferably but not exclusively a mixture of liquid crystalline materials selected so that the observed colour or colour gradient changes provide an indication of the temperature of the adjacent environment within a predetermined accuracy over a defined temperature range. A suitable temperature range for wound monitoring may be 25° to 45° C. but is not limited to this range. Suitable liquid crystalline materials are cholesterol based compounds but may also be non-sterol in nature.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The invention will now be further described, by way of example only, with reference to the accompanying drawings, in which:

FIG. 3 is a simplified cross-section of the die of the arrangement illustrated in FIG. 2;

FIG. 4 is a plot of the reflectance spectra in the visible range as a function of temperature for composite sensor fibres incorporating a particular mixture of cholesterol based liquid crystalline materials.

DETAILED DESCRIPTION OF EMBODIMENTS OF THE INVENTION

Figure 1:
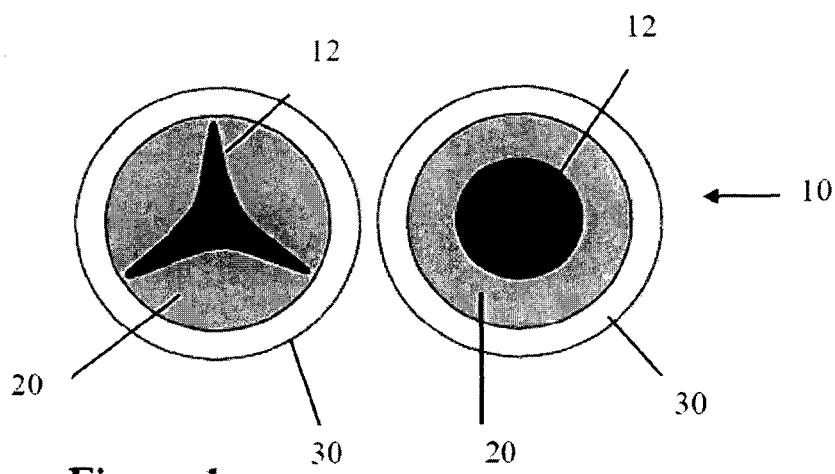
FIG. 1 is a diagram of alternative idealised cross-sections of embodiments of composite sensor fibre according to the first aspect of the invention.

FIG. 1 shows two preferred but non-limiting alternative cross sections for composite sensor fibres 10 according to the invention. Each fibre comprises a solid filamentary core 12 and an outer layer 30 encapsulating an intermediate sensor layer 20 of a detectably thermoresponsive material. Outer layer 30 is of generally tubular configuration. In one case, the core is of solid cylindrical form while in the other the core is symmetrically trilobal. Both illustrations are idealised: real fibres approximate these forms.

A particularly useful form of the composite sensor fibre is one in which the intermediate sensor layer 20 comprises thermochromic material, the core 12 provides a contrast for facilitating visibility of colour and/or colour gradient changes in the intermediate layer, and the outer layer 30 is substantially transparent for viewing those colour or colour gradient changes. In embodiments of particular interest, the core 12 is a polymer containing black or dark pigment and the intermediate sensor layer 20 is a thermochromic liquid crystalline mixture. Such a fibre reversibly changes colour through the full visible spectrum from red to blue as the temperature is increased through a working temperature range determined by the composition of the liquid crystalline mixture. Consistent with the general behaviour of unencapsulated thermochromic liquid crystalline mixtures, the fibre exhibits clear and reversible thermochromic behaviour.

The filamentary core 12 may be a monofilament or multifilament fibre, preferably made from a high temperature stability polymer or metal in view of the process of formation as described below. A particularly suitable such polymer is polyether ether ketone (PEEK) containing black or dark pigment. The core preferably though not essentially provides mechanical support for the further layers of the fibre.

In the case where the intermediate layer 20 is a thermochromic material, the trilobal shape of FIG. 1 is preferred because this maximises the contrast background when viewed from any given angle without compromising the flowability of the material in the later described coextrusion process for formation of the composite fibre. In this case, the intermediate layer 20 is divided into three longitudinal segments and the core 12 contacts the outer layer 30 at the tip of each lobe, and is thereby anchored to the outer layer.

In the simplest case, however, the core 12 may be generally circular in cross-section. In other embodiments, it may be, for example, linear or elongated with flat sides, or elliptical, or, in more complex shapes, quadralobal, hexalobal, etc.

The intermediate sensor layer may in general be a liquid, a low melting point wax, or a solid at room temperature. The preferred liquid crystalline mixtures are waxy or oily at room temperature, 20° C.

Figure 2:
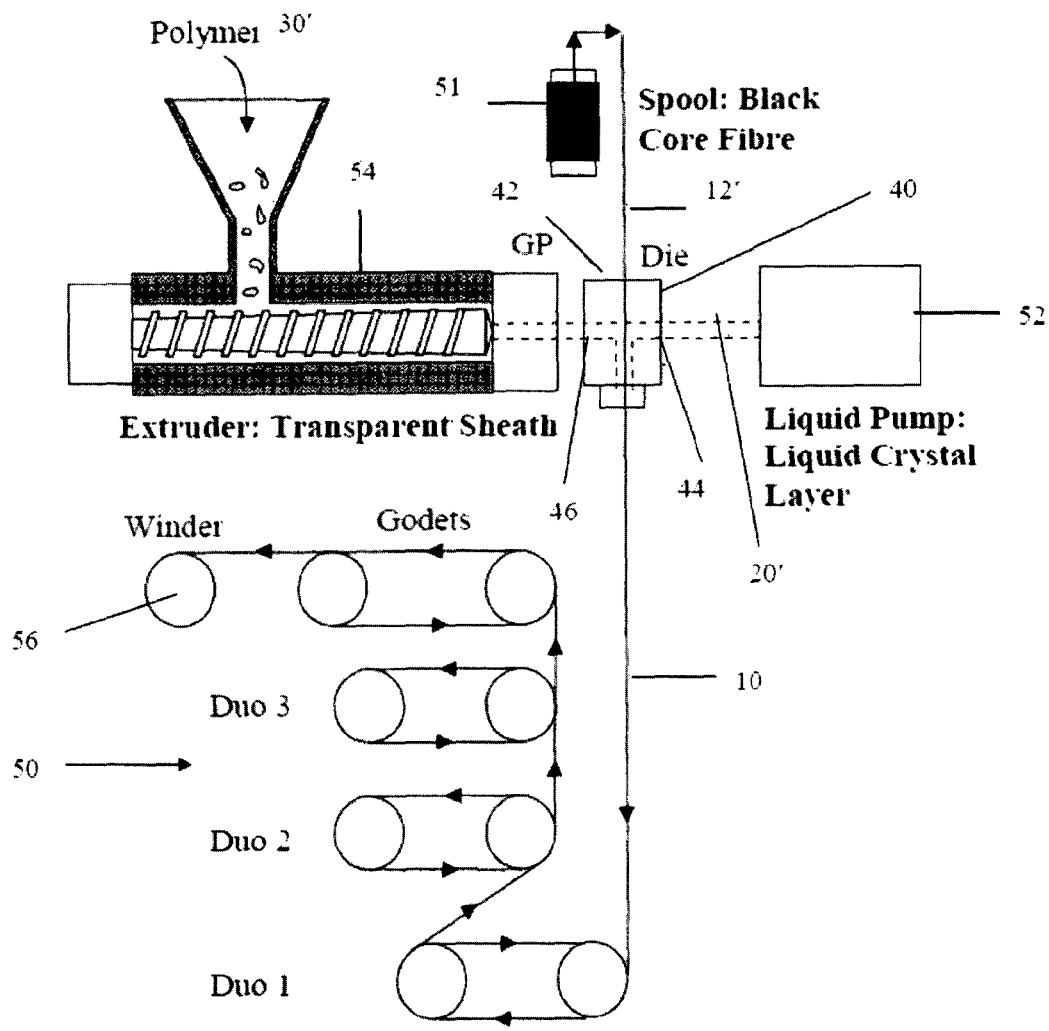
FIG. 2 is a schematic of a suitable melt extrusion arrangement for forming composite sensor fibres such as those depicted in FIG. 1.

A preferred process for forming the composite, sensor fibre of the invention, in particular the preferred composite thermochromic fibre, is a melt coextrusion process. A schematic of the setup for this process is provided in FIG. 2. The three components are fed simultaneously into a die 40 configured for "wire strand coating" coextrusion. A simplified cross-sectional profile of a successful die configuration is shown in FIG. 3.

A pre-prepared high melting temperature polymer fibre/filament 12' containing black pigment (for example PEEK containing carbon black pigment) is threaded vertically through the die 40 via feed point 42 and drawn through from a supply spool 51 at a steady rate as controlled by a downstream godet system 50. At the same time a pre-prepared thermochromic liquid crystalline mixture 20' is fed at a steady rate into feed point 44 from a liquid pump 52, and an appropriate polymer 30' is fed at a steady rate as a melt into feed point 46 by a melt extruder 54.

An example of a suitable polymer for the outer transparent layer is polypropylene, which has a melting temperature substantially lower than the inner core material, for example, below 200° C., and was found to perform very well in the illustrated setup. PEEK has a melting temperature of 343° C.

The liquid pump 52 is maintained at a temperature to enable the liquid crystal mixture to flow sufficiently, for example in the range 40-80° C.

The liquid crystalline and polymer layers are coated onto the core fibre 12' as it passes through the die by co-extrusion of the thermochromic liquid crystalline material 20' about the core 12' and of the outer layer 30' about the liquid crystalline material 20'. On exiting the die at 48 the outer polymer layer solidifies and traps the thermochromic intermediate layer between the core fibre and itself. The resultant composite fibre 10 is then passed through the godet system 50 (which may or may not involve further elongation) and is collected at the winder onto a bobbin 56.

The PEEK fibre/filament 12' is drawn/pulled through by the godet system. The liquid crystalline material and polymer melt are simultaneously fed into the die at rates dependent on the throughput speed of the PEEK fibre and the desired loadings. The rate of release of the liquid crystalline material is controlled by the liquid pump 52. The composite sensor fibre formed typically has a diameter in the range 5 to 300 micrometers, preferably 30 to 300 micrometers, most preferably 60 to 300 micrometers, but not limited to these ranges, depending on the relative amounts of each component in the cross-sectional profile.

During the above process conditions are maintained to ensure a substantially even coating of both components onto the outside of the PEEK fibre. If the die is too cool for example, the polypropylene melt blocks the progress of liquid crystalline material out of the die between the two polymer layers. Thus the temperature of the die is set in a range that facilitates the co-extrusion but at which the core remains substantially solid (and therefore typically suffers little or no distortion), and the outer layer does not inhibit delivery of the liquid crystalline material. A suitable temperature range that meets these requirements for the described feed components is found to be above the melting temperature of the outer material but below the melting temperature of the inner core material, for example in the range 170° C. to 200° C.

Applications of composite fibres according to the first aspect of the invention include temperature indicator devices for thermal mapping of both engineering surfaces, for example building surfaces (walls, floors and ceilings), wires, cables and pipes, and human body surfaces. A particularly useful application of the illustrated composite fibre, in accordance with the second aspect of the invention, is a wound dressing. In one embodiment, the composite fibre 10 may be woven or knitted into a tubular wound dressing of varying diameter, e.g. between 2 mm and 10 cm. For this application the thermochromic material of the intermediate sensor layer 20 is tuned to have a working temperature anywhere within the "pathological" temperature range 25-45° C. In more specialist applications, e.g. frostbite patients, the working temperature would be suitably adapted. As a wound dressing, the fibre enables clinicians and patients themselves to monitor, observe or map the temperature distribution across and around wound beds, especially chronic wounds such as leg ulcers, pressure ulcers and diabetic food ulcers, while the dressing is being worn. This type of system is advantageous in that it does not rely on the use of any electronic equipment or probes, which can be invasive, expensive and otherwise impractical. Temperature indication can be achieved by comparing the localised colour observed within the thermochromic fibres with a calibrated colour temperature chart. Absolute temperatures can be recorded as well as temperature differences or gradients between different areas of a wound bed and undamaged surrounding tissue. The observed colour or colour gradient should ideally give an accurate indication of the temperature of the surrounding environment within 0.1 and 0.5° C. over a defined pathological temperature range, e.g. the aforementioned 25° C. to 45° C., or a more focused range e.g. 27-37° C. or 33-37° C.

Temperature monitoring of wounds can aid in the early detection of problems such as harmful inflammation and infection (typically accompanied by a local increase in temperature), or tissue necrosis and interruptions of blood supply to tissue (typically accompanied by a local decrease in temperature). Early detection of developing problems can lead to more relevant treatment of wounds and therefore faster wound closure.

Other applications for thermochromic fibrous material include garments such as stockings or socks for the temperature monitoring of undamaged skin deemed to be at risk of developing a chronic wound such as a venous leg ulcer, with the hope that the wound formation may be prevented altogether in some cases.

By careful selection of a liquid crystalline mixture, the material appears red at the lower range of its working temperature range and the colour shifts through the full visible spectrum (red to yellow to green to blue) as the temperature increases. The behaviour is completely reversible.

Liquid crystalline mixtures that have been found to be satisfactory are mixtures of cholesterol based compounds including cholesteryl oleyl carbonate (COC), cholesteryl nonanoate (CN) and cholesteryl 2, 4-dichlorobenzoate (CD). Acceptable mixtures include:
  i 50% COC, 40% CN, 10% CD
  ii 40% COC, 40% CN, 20% CD
  iii 30% COC, 40% CN, 30% CD Other relevant cholesterol based derivatives include but are not limited to cholesteryl benzoate, cholesteryl propionate, cholesteryl oleate, and cholesteryl chloride. The mixture can be prepared by weighing two or more cholesterol based derivatives into a glass vessel and heating to 90-110° C. with mixing until all components melt and combine to form a homogenous clear liquid. The resultant mixture develops a thick and oily consistency when cooled to room temperature. The compounds chosen and their relative amounts determine the working temperature range of the thermochromic mixture. Other suitable mixtures include both cholesterol based and non sterol based compounds.

It has been established that these liquid crystalline mixtures are not dramatically changed, in respect to their thermochromic responses, by their passage through the die and resultant trapping between the PEEK and polypropylene polymer layers.

FIG. 4 shows how the reflectance spectra in the visible range shifts from the red end of the spectrum to the blue as the temperature is increased for the liquid crystalline mixture (ii) above. The behaviour has been found to compare well to that of the unincorporated mixture and is reversible.

Figure 5:
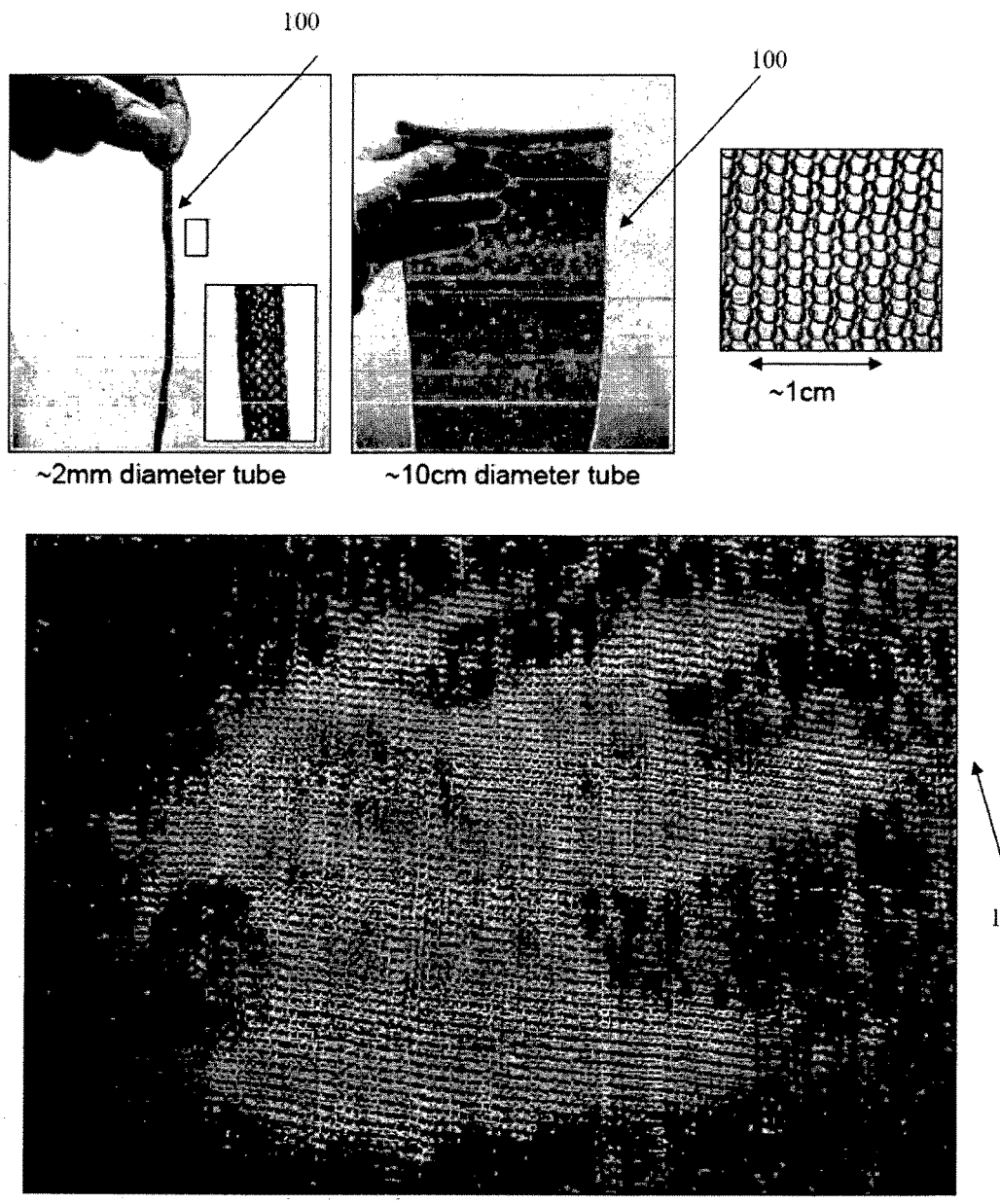
FIG. 5 depicts (by greyscale shading) the thermochromic response to the application of a warming human hand to a fabric knitted from composite thermochromic fibres similar to that having the response characteristic illustrated in FIG. 4.

Composite thermochromic fibre comprising a PEEK core, liquid crystalline mixture (ii) and a polypropylene outer layer was knitted into a tubular fabric dressing of varying diameters from 2 mm to 10 cm. FIG. 5 shows the fabric 100, and depicts (by greyscale shading) the thermochromic response to the application of a warming human hand to the fabric.

The invention claimed is:

1. A composite sensor fibre comprising a filamentary core and an outer layer encapsulating an intermediate sensor layer of a flowable and detectably thermochromic liquid crystalline material between the filamentary core and the outer layer, the thermochromic liquid crystalline material comprising at least one selected from cholesteryl oleyl carbonate, cholesteryl nonanoate, cholesteryl 2, 4-dichlorobenzoate, cholesteryl benzoate, cholesteryl propionate, cholesteryl oleate, and cholesteryl chloride, wherein the outer layer is transparent and the filamentary core is configured to provide a contrast for facilitating the observation of temperature or temperature gradient changes in the thermochromic liquid crystalline material, and wherein the temperature or temperature gradient changes comprise changes in color or color gradient.

2. A composite sensor fibre according to claim 1 wherein the thermochromic liquid crystalline material is a mixture of liquid crystalline compounds selected to achieve a predetermined temperature indication accuracy over a predetermined temperature range.

3. A composite sensor fibre according to claim 1 wherein the filamentary core is of a cross-section selected from generally circular and generally trilobal sections.

4. A composite sensor fibre according to claim 1, wherein the outer layer has a melting temperature below that of the filamentary core.

5. A composite sensor fibre according to claim 1 wherein the filamentary core is a monofilament or multifilament fibre.

6. A composite sensor fibre according to claim 1, wherein the filamentary core is polyester ether ketone (PEEK).

7. A fibrous material formed from or incorporating composite sensor fibres according to claim 1.

8. A fibrous material according to claim 7 comprising a fabric.

9. A clothing item that includes fibrous material according to claim 8.

10. A method of making a composite sensor fibre according to claim 1, comprising continuously delivering the filamentary core from a supply thereof and co-extruding the thermochromic liquid crystalline material about the core and the outer layer about the thermochromic liquid crystalline material at a temperature that facilitates the coextrusion but at which the core remains substantially solid and the outer layer does not inhibit delivery of the thermochromic liquid crystalline material.

11. A method according to claim 10, wherein the thermochromic liquid crystalline material is a mixture of liquid crystalline compounds selected to achieve a predetermined temperature indication accuracy over a predetermined temperature range.

12. A method according to claim 11, wherein the mixture of liquid crystalline compounds is fed by a pump at an elevated temperature selected to enable the mixture to flow at the elevated temperature.

13. A dressing that includes a fabric having a matrix of thermochromic composite sensor fibres according to claim 1, which fibres indicate localised body temperature changes adjacent the dressing by visibly exhibiting a change in colour or colour gradient.

14. A dressing according to claim 13 wherein the composite sensor fibres are selected whereby localised body temperature changes adjacent to the dressing within the range 25° C. to 45° C. are visibly exhibited by a change in colour or colour gradient.

15. A dressing according to claim 14, wherein the thermochromic liquid crystalline material of the composite sensor fibres is a mixture of liquid crystalline compounds selected to achieve a predetermined temperature indication accuracy within the temperature range 25° C. to 45° C.

16. A method of monitoring a wound comprising applying to the wound a dressing that includes a fabric having a matrix of thermochromic composite sensor fibres according to claim 1, which fibres indicate localised body temperature changes adjacent the dressing by visibly exhibiting a change in colour or colour gradient.

17. A method according to claim 16 wherein the composite sensor fibres of the fabric are selected whereby localised body temperature changes adjacent to the dressing within the range 25° C. to 45° C. are visibly exhibited by a change in colour or colour gradient.

18. A method according to claim 17, wherein the thermochromic liquid crystalline material of the composite sensor fibres is a mixture of liquid crystalline compounds selected to achieve a predetermined temperature indication accuracy within the temperature range 25° C. to 45° C.

19. A method according to claim 18 wherein said mixture of liquid crystalline compounds is a mixture of cholesterol based compounds.

* * * * *